(12) United States Patent
Theobald

(10) Patent No.: US 10,028,878 B1
(45) Date of Patent: Jul. 24, 2018

(54) BODY WORN APPARATUS

(71) Applicant: Daniel Theobald, Somerville, MA (US)

(72) Inventor: Daniel Theobald, Somerville, MA (US)

(73) Assignee: VECNA TECHNOLOGIES, INC., Cambridge, MA (US)

(*) Notice: Subject to any disclaimer, the term of this patent is extended or adjusted under 35 U.S.C. 154(b) by 661 days.

(21) Appl. No.: 13/687,293

(22) Filed: Nov. 28, 2012

(51) Int. Cl.
*A61H 1/02* (2006.01)
*A61H 9/00* (2006.01)
*A61H 31/00* (2006.01)

(52) U.S. Cl.
CPC ............ *A61H 1/02* (2013.01); *A61H 1/024* (2013.01); *A61H 1/0277* (2013.01); *A61H 9/0078* (2013.01); *A61H 31/00* (2013.01); *A61H 2201/1238* (2013.01); *A61H 2201/165* (2013.01)

(58) Field of Classification Search
CPC ........ A61H 9/00; A61H 9/005; A61H 9/0078; A61H 9/0085; A61H 9/0092; A61H 31/02; A61H 2201/1238; A61H 2201/1246; A61H 2201/1409; A61H 1/0237–1/0296; A61H 2003/007; A61H 2205/081; A61F 2002/74–2002/748
See application file for complete search history.

(56) References Cited

U.S. PATENT DOCUMENTS

| | | | | |
|---|---|---|---|---|
| 4,671,258 A | * | 6/1987 | Barthlome | A61H 1/0288 128/DIG. 20 |
| 4,739,692 A | * | 4/1988 | Wassam | B25J 9/06 901/21 |
| 5,040,626 A | | 8/1991 | Paynter | |
| 5,080,000 A | | 1/1992 | Bubic | |
| 5,351,602 A | | 10/1994 | Monroe | |
| 5,529,293 A | | 6/1996 | Haugs | |
| 6,168,634 B1 | * | 1/2001 | Schmitz | B25J 9/1075 414/4 |
| 6,698,510 B2 | * | 3/2004 | Serra | A41D 13/005 165/10 |
| 7,104,182 B2 | | 9/2006 | Reininger | |
| 7,331,273 B2 | | 2/2008 | Kerekes | |
| 7,837,144 B2 | | 11/2010 | Kothera | |
| 9,506,481 B1 | | 11/2016 | Theobald | |
| 2001/0029343 A1 | * | 10/2001 | Seto | A61F 2/54 600/587 |
| 2002/0157322 A1 | | 10/2002 | Pedretti | |
| 2002/0157388 A1 | | 10/2002 | Seto | |
| 2005/0126578 A1 | * | 6/2005 | Garrison | A61H 9/0078 128/874 |
| 2006/0161220 A1 | * | 7/2006 | Kobayashi | A61F 5/0102 607/49 |
| 2007/0129653 A1 | * | 6/2007 | Sugar | A61H 1/02 601/5 |
| 2009/0173223 A1 | | 7/2009 | Kudawara | |
| 2009/0276058 A1 | * | 11/2009 | Ueda | A61H 1/0274 623/57 |
| 2010/0249675 A1 | * | 9/2010 | Fujimoto | A61H 1/0285 601/40 |

(Continued)

*Primary Examiner* — Valerie L Woodward

(57) ABSTRACT

A method and apparatus provides a body worn apparatus having a plurality of activation elements arranged in at least one bundle, and a substrate supporting the plurality of activation elements. The method also places the body worn apparatus onto the body of a person, and activates the at least one bundle.

1 Claim, 4 Drawing Sheets

(56) References Cited

U.S. PATENT DOCUMENTS

| | | | | |
|---|---|---|---|---|
| 2010/0256540 | A1* | 10/2010 | Yamashiro | A61H 9/0078 601/44 |
| 2011/0023474 | A1* | 2/2011 | Kudawara | B25J 9/1075 60/325 |
| 2011/0313331 | A1* | 12/2011 | Dehez | A61H 1/0277 601/33 |
| 2012/0184881 | A1* | 7/2012 | Kobayashi | A61F 5/01 601/33 |
| 2012/0238914 | A1* | 9/2012 | Goldfield | A61B 5/6804 600/595 |
| 2014/0238153 | A1* | 8/2014 | Wood | G06F 3/011 73/862.627 |
| 2015/0088043 | A1* | 3/2015 | Goldfield | A61F 5/01 602/6 |

* cited by examiner

| Property | Human Muscle | Hydraulics |
|---|---|---|
| Max. Strain (L/L$_0$) | 30-70% | 10-100% |
| Max. Stress (MPa) | .1-.4 | 20-70 |
| Power Density (W/m$^3$) | $5 \times 10^5$ | $5 \times 10^8$ |
| Density (kg/m$^3$) | 1000-1100 | 1600-2000 |
| Efficiency | 20-25% | 90-98% |
| Activation Frequency (s$^{-1}$) | 5 - 500 | 5 - 300 |
| Control Resolution | $10^{-1}$-$10^{-2}$ | $10^{-5}$-$10^{-4}$ |

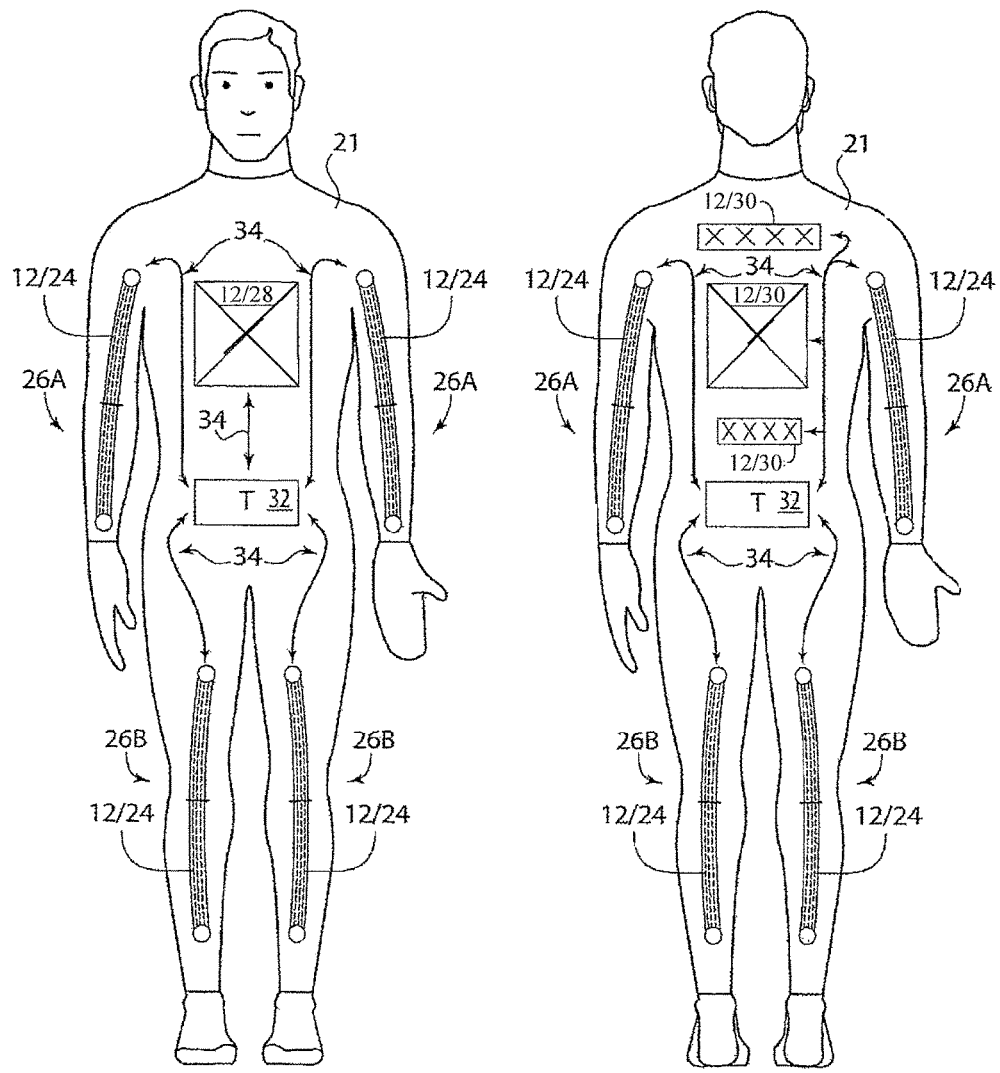

US 10,028,878 B1

BODY WORN APPARATUS

FIELD OF THE INVENTION

The present invention relates generally to actuators and, in at least one embodiment, to such actuators that are hydraulic or fluid powered and/or used as an artificial or "mechanical" muscle and used in a body worn apparatus.

BACKGROUND OF THE INVENTION

Actuators typically are mechanical devices that are used for moving or controlling a mechanism, system or the like and typically convert energy into some type of motion. Examples of actuators can be found in any number of applications encountered in everyday life including automotive, aviation, construction, farming, factories, robots, health care and prosthetics, among other areas.

Mobile robotics and advanced prosthetics will likely play important roles in the future of the human race. Actuators frequently are used in these applications that enable movement of a robot or user arm or other appendage or item as desired.

Most existing mobile robots and advanced prosthetics, however, lack the strength and speed necessary to be effective. This is because they suffer from poor specific power (strength×speed/weight) which determines how quickly work can be done compared to another actuator of the same weight.

For example, if such devices are capable of lifting significant weight, they must do so very slowly, which inhibits their adoption for most applications. On the other hand, devices that can move more quickly are just not capable of handling anything more than the smallest weight.

Hydraulic and pneumatic power systems can be used with such actuators, among other power systems. Pneumatic power systems, however, have a relatively low operating pressure, which limits the amount of force they can impart and exhibit poor controllability due to the compressible nature of air, among other drawbacks.

Additionally, conventional hydraulics technology suffers from poor efficiency, noisy operation, high cost and maintenance challenges among other problems. These and other problems inhibit the use of hydraulics in many applications.

SUMMARY OF THE INVENTION

In accordance with one embodiment of the invention, a method and apparatus provides a body worn apparatus having a plurality of activation elements arranged in at least one bundle, and a substrate supporting the plurality of activation elements. The method also places the body worn apparatus onto the body of a person, and activates the at least one bundle.

BRIEF DESCRIPTION OF THE DRAWINGS

The following detailed description will be better understood when read in conjunction with the appended drawings in which there is shown one or more of the multiple embodiments of the present disclosure. It should be understood, however, that the various embodiments of the present disclosure are not limited to the precise arrangements and instrumentalities shown in the drawings.

FIG. 4 is a partial cross-sectional view of one embodiment of the present invention illustrating a plurality of activation elements enclosed in an outer sheath member or the like;

FIG. 8 is a schematic front view of a body worn apparatus configured in accordance with illustrative embodiments of the invention.

FIG. 9 is a schematic rear view of the body worn apparatus of FIG. 8.

DETAILED DESCRIPTION OF THE INVENTION

Figure 1:
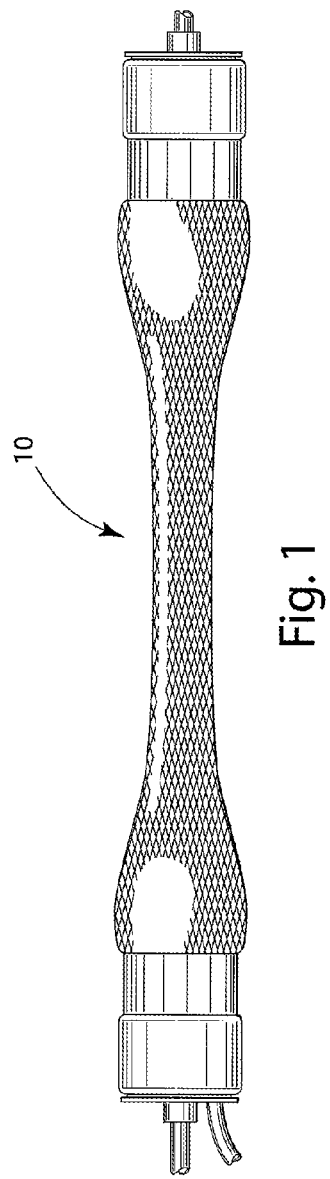
FIG. 1 is a plan view of one embodiment of an activation element of the present invention that may be utilized with the actuator of the present invention illustrated in a first "at rest" position.

Various embodiments of the present invention are described below with reference to the accompanying drawings. It should be understood that the following description is intended to describe exemplary embodiments of the invention, and not to limit the invention.

It is understood that the present invention is not limited to the particular components, analysis techniques, etc. described herein, as these may vary. It is also to be understood that the terminology used herein is used for the purpose of describing particular embodiments only, and is not intended to limit the scope of the present invention. It must be noted that as used herein, the singular forms "a," "an," and "the" include plural reference unless the context clearly dictates otherwise. The invention described herein is intended to describe one or more preferred embodiments for implementing the invention shown and described in the accompanying figures.

Unless defined otherwise, all technical and scientific terms used herein have the same meanings as commonly understood by one of ordinary skill in the art to which this invention belongs. Preferred methods, system components, and materials are described, although any methods and materials similar or equivalent to those described herein can be used in the practice or testing of the present invention.

Many modifications and variations may be made in the techniques and structures described and illustrated herein without departing from the spirit and scope of the present invention. Accordingly, the techniques and structures described and illustrated herein should be understood to be illustrative only and not limiting upon the scope of the present invention. The scope of the present invention is defined by the claims, which includes known equivalents and unforeseeable equivalents at the time of filing of this application Various embodiments of the present invention are directed to various devices that are fluid powered, such as by hydraulics or pneumatics, for example. It is to be understood, however, that some embodiments of the present invention are not limited to these two specific technologies.

In operating a robot, advanced prosthetic, or some other item or mechanism, some type of power system typically is provided to enable particular movement, such as moving an arm or other appendage, for example. As readily can be discerned, in order to provide at least up and down movement to an arm member or the like some type of mechanical or other actuator typically is employed.

In a simple example, a piston driven actuator may be implemented to accomplish this movement. By moving the piston back and forth within a cylinder, the piston rod provides the basic movement to the arm member connected at is distal end.

Another type of actuator can be one that mimics the motion of a real biological muscle in the body of a human or other animal. These artificial or mechanical muscles typically provide some type of expandable member or tube connected at one end to an arm member, such as a forearm of a robot, for example, and at the other end to another member such as the upper arm or shoulder of a robot, for example.

Briefly, in operation, when such a member is expanded in a direction substantially perpendicular to its longitudinal centerline, it essentially contracts the member thereby drawing the arm closer to the shoulder. When the member is thereafter allowed to expand in a direction substantially parallel to its longitudinal centerline, it essentially extends the member and the arm moves away from the shoulder.

One example of such a mechanical muscle is known as a McKibbons style actuator, which is hereby incorporated by reference. It is to be understood, however, that the particular type of mechanical muscle and corresponding expanding member can vary without departing from the teachings of various embodiments of the present invention.

These types of actuators or mechanical muscles exhibit a specific power (strength x speed/weight) that far exceeds that of existing actuators typically used in robots that suffer from poor efficiency, noisy operation, high cost and maintenance challenges, among other drawbacks. These drawbacks and more are readily solved by the design of illustrative embodiments of the present invention that readily exceed the performance of real biological muscles.

Additionally, as the human race begins to work in close collaboration with robots, advanced prosthetics, and similar machines and mechanisms, they are anticipated to expect the robots to be stronger, faster, have better endurance, be more precise, and cost less than other options. They also may expect robots to quickly and efficiently carry out their assigned physical tasks with little or no down time for maintenance or fatigue, for example.

Biological muscles consist of many smaller "actuator" fibers called sarcomeres, bundled in parallel. During movement of a body limb, for example, all or just a partial subset of available fibers may be activated depending on the task involved.

By scaling down the size of mechanical muscles, arranging them in bundles and designing them to handle much higher hydraulic pressures, a large increase in specific power is achieved. Significant reduction in the overall weight of this design, among other factors, leads to this increase in specific power. At the same time, by activating any number of the actuators arranged in such a bundle to vary the power output for the task at hand, significant power savings is achieved.

When employing these types of mechanical or artificial muscles, the trend is to provide a single actuator for each direction of desired motion. With this design, variations in movement and control are limited.

One key feature among many of illustrative embodiments is to provide a plurality of discrete, readily interchangeable mechanical muscles for each direction of desired motion, where each muscle has a predetermine power capability. This concept dramatically teaches away from conventional thinking, provides a number of distinct and unexpected results and advantages in the art, and essentially revolutionizes the potential applications possible.

As one example, by using a plurality or bundle of muscles, the number of muscles activated can vary depending on the power requirements of the task at hand. One advantage of this novel design concept is power conservation, which is particularly important with mobile robots as well with overall environmental concerns.

Another advantage is in the type and number of potential applications that become available by using a bundle of muscles. With conventional thinking being to merely increase the size of the actuator or muscle to increase the power capability of the device, applications are limited to larger and larger devices. In the design discussed herein, smaller and smaller applications are possible since the actuators can be smaller and lighter, among other attributes.

Examples of various hydraulic systems and robotic applications where a mechanical muscle may be employed can be found, for example, in applicant's issued U.S. Pat. No. 7,348,747 filed Mar. 30, 2006, issued U.S. Pat. No. 7,719,222 filed Mar. 24, 2008 and pending U.S. patent application Ser. No. 12/731,270 entitled "Task Flexibility for Actuators" filed Mar. 25, 2010 and related co-pending applications, all of the disclosures of which are hereby incorporated by reference. It is to be understood, however, that the particular details of the hydraulic system itself, as well as the robot, vehicle, tool, heavy equipment, actuator, or other apparatus, can vary without departing from the teachings of various embodiments of the invention.

Figure 2:
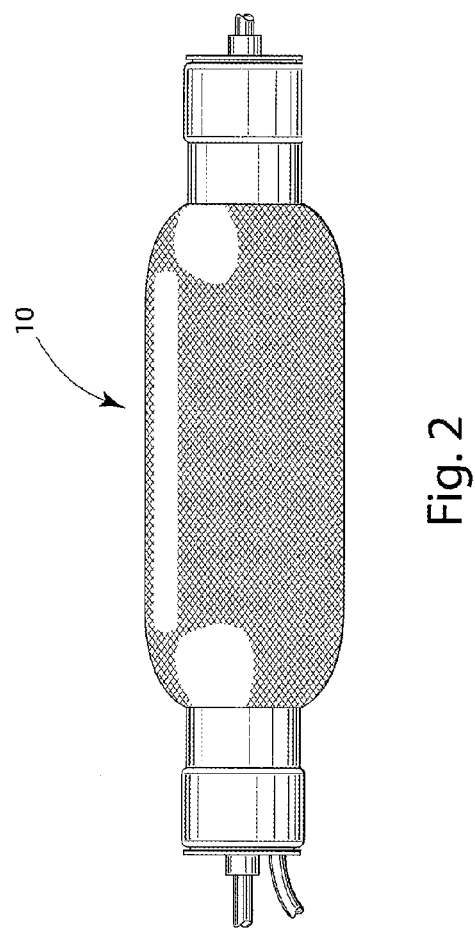
FIG. 2 is a plan view of the element of FIG. 1 illustrated in a second activated position.

FIGS. 1 and 2 generally illustrate one embodiment of a mechanical muscle 10 (i.e., an activation element) that may be employed in various embodiments of the present invention. The particular size, shape, material and design of the muscle 10 can vary so long as it falls within the scope of the appended claims.

Briefly, in operation, FIG. 1 generally illustrates the muscle 10 in an extended or at-rest position where no fluid is provided to the interior of the muscle 10. As FIG. 2 generally illustrates, when fluid is provided to the interior of the muscle 10, the muscle 10 expands in a direction substantially perpendicular to its longitudinal centerline, essentially contracting the muscle 10, thereby shortening it length. Conversely, when fluid is essentially released from the interior of the muscle 10, the muscle 10 expands in a direction substantially parallel to its longitudinal centerline, thereby increasing its length.

As readily can be discerned and described in more detail below, if the muscle 10 is attached on opposite ends to other members, desired movement between the members can be achieved. Additionally, the particular type, shape, material and design of the muscle 10 can be varied to in turn vary the movement between the two members to which it is attached.

Figure 3:
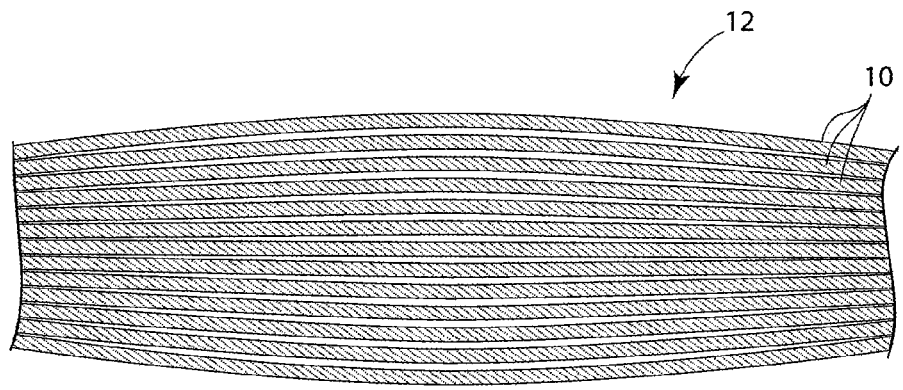
FIG. 3 is a partial plan view of one embodiment of the present invention illustrating a plurality of activation elements arranged in a bundle.
Figure 4:
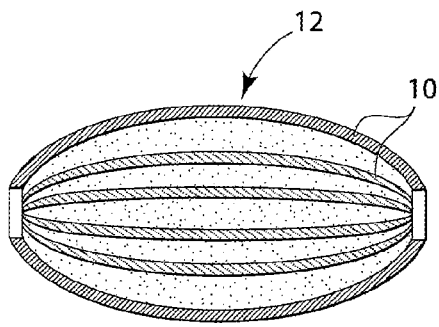
Figure 5:
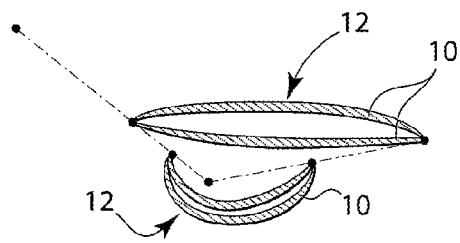
FIG. 5 is a semi-schematic view of one embodiment of the present invention illustrating one potential use of the activation elements.

As FIG. 3 generally illustrates, the number of muscles 10 utilized can be expanded to vary the performance of the muscle 10 as needed. In particular, by providing a number of muscles 10 in one or more bundles 12 a corresponding increase in the lifting or movement capacity of the muscle 10 or bundle 12 can be accomplished.

Existing actuators for robot, prosthetics, and the like are heavy and lack the specific power necessary for effective designs. This limits the number, strength, and speed of each degree of freedom in a robot or the like.

While the human body has over 600 individual skeletal muscles, the most advanced humanoid robots in existence today can afford only 50 or so conventional actuators and still end up weighing twice as much as a human, which can present a safety issue when working closely with humans. To be truly capable and safe, robots and prosthetics need to be stronger, weigh less, and have many more degrees of freedom than current systems.

Pneumatic actuators or mechanical muscles are limited by their relatively low operating pressure of about 100 PSI and poor controllability due to the compressible nature of air, which is generally the working fluid in such pneumatic systems. By utilizing a design incorporating hydraulically actuated actuators or mechanical muscles as described herein that are capable of operating at much higher pressures of about 3000 PSI, incredible increases in power are provided while increasing controllability.

As the goal of robotics aims to supplant human labor, human skeletal muscle is an appropriate standard to beat. Muscles provide adaptive, integrated closed-loop positional control; energy absorption and storage; and elastic strain to allow for deformation of tissue under loads. They are rapidly responsive and able to adjust spring and damping functions for stiffness and compliance in stability, braking, and more. A viable artificial actuation approach should at least provide such comprehensive functionality; additionally such an approach should meet or exceed the set of performance metrics of human muscles and improve upon muscles' limited peak performance envelope.

Figures 6, 7:
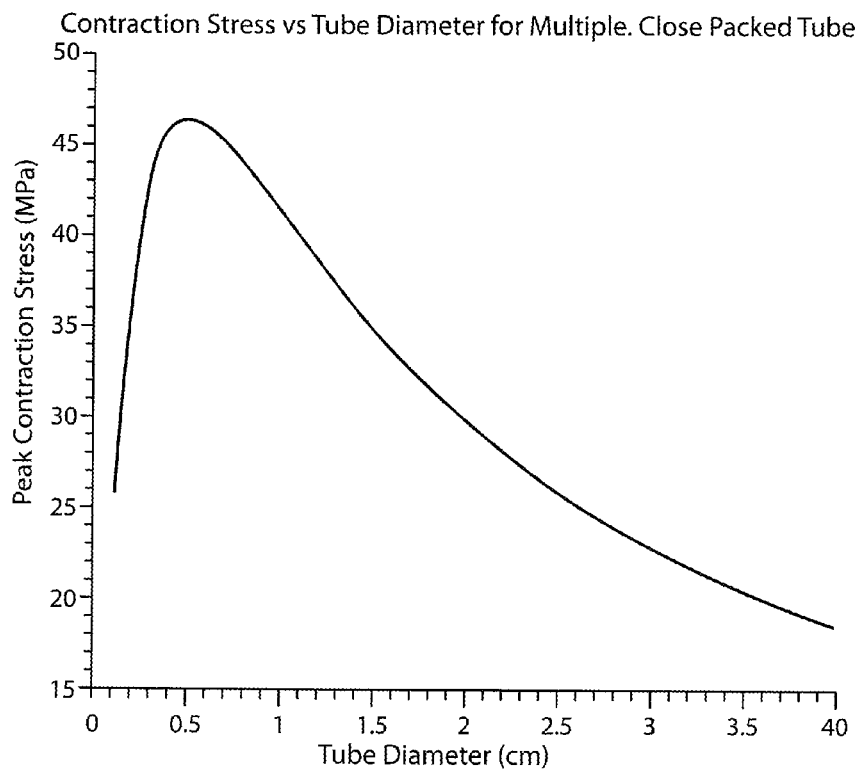
FIG. 6 is a table illustrating performance characteristics of human muscles and hydraulic systems.
FIG. 7 is a graph illustrating contraction stress vs. tube diameter.

As FIG. 6 illustrates, hydraulic mechanical muscles 10 outperform human muscle in power density, efficiency, stress vs. strain, frequency, control resolution, and will closely match human muscle in density, and variable compliance ability. In addition, hydraulic mechanical muscles will also achieve significant improvements in the state of the art in terms of cost, manufacturability, flexibility in application, and scalability. As described earlier, the power density factor is an important criterion that implies the simultaneous speed and strength needed for things like running and throwing.

While existing somewhat exotic actuator technologies may exceed any single actuator performance metric, they are unable to provide comparable overall performance. For example, piezoelectrics are unacceptably brittle; shape memory alloys (SMAs) have prohibitively slow response cycles due to a temperature-dependent actuation; magnetostrictors require constant, fragile magnetic fields at large scales.

Additionally, electroactive polymers (EAPs), require large and potentially unsafe actuation voltages (>1 kV, typical) and consistent current to maintain displacement, possibly making them unacceptably inefficient while chemically-activated ionic versions do not consistently sustain DC-induced displacement and have slow response times. Additionally, EAPs have difficulty damping for low frequency vibration and inaccurate position sensing capabilities due to inherent actuator flexibility. Since biological joints are analogous to direct-drive actuation and therefore largely backdrivable (i.e. resilient), the same forces acting upon an EAP actuator in a leg for example will cause it to deform and perform unexpectedly. Most of all, these materials are prohibitively expensive and complicated to manufacture.

More conventional existing actuators fail to replicate muscle-like performance for a number of reasons. Electromagnetic approaches lack any real scalability because of their need for expensive, high power, rare-earth magnets. Their highly specialized motor design precludes the force output properties of muscle tissue.

Out of all available actuation techniques, pneumatic actuators, particularly of the "mechanical muscle" or McKibbens type described above appear to most closely match the force-velocity and force-length characteristics of human muscle. These pneumatic actuators exploit the high power density, light weight, and simplicity of fluid power, but precise control of these systems is difficult because of the compressibility of air and the inherent excessive compliance, hysteresis, nonlinearity, and insufficient contraction rates of rubber actuators.

In contrast, a hydraulic approach to mechanical muscle fluid power avoids these limitations while at the same time offering inherent advantages for adjustable compliance, proportional force output, energy recovery and efficiency, precise control, and scalability. This broad complement of properties makes hydraulics an excellent candidate for biometric actuation.

In fact, the overall superior performance of hydraulics for vibration damping, actuation frequency, and volumetric power for compact designs in general applications are well known. Furthermore, since hydraulics operate on virtually the same principles as pneumatics, which perform comparably to natural muscle, they are similarly suitable for artificial muscles if used in the right actuator design. As such, a new paradigm in actuator approach is provided in at least one embodiment of the present invention that leverages the superior power and controllability of hydraulics with biophysical principles of movement.

One of the many significant benefits of a bundle of mechanical muscles approach is that simultaneous activation of all of the bundled actuators becomes unnecessary; rather, there is the potential to activate only the minimum of muscle fibers or actuators that are needed for the task. Benchtop tests demonstrated a 3 inch displacement for a strain of 70%. Maximum pulling force (before material failure) was approximately 95 pounds at a pressure of nearly 1800 PSI. This bundle approach to mechanical muscles will achieve at least 10 times the specific power of human muscle while achieving similar impedance control, and will be practical for use in robotic systems. As this type of system is perfected, additional increases in specific power are anticipated.

Human muscle is comprised of both pennate (fibers aligned at an angle to the muscle's long axis) and parallel-fibred muscles, each with functionally-specific mechanical features: pennate muscles act around joints, rotating their angle to act as variable gears, while parallel-fibered muscles are the workhorses (cf. biceps brachii or soleus) of load-bearing movement. The mechanical advantage of a bundle of small or miniature McKibbons type actuators is similar: since Pascal's Law holds that increases in fluid pressure are distributed equally to all parts of a system, force increases proportionally with the cross-sectional area of the actuator. Since it has been identified that adjustable force output can be a function of increased actuator diameter, using bundles or clusters of miniature McKibbons type actuators can scale upward in cross-sectional area through the addition of more actuators; since the individual actuator size does not increase, tolerances for pressure and stress remain the same while force output increases.

In a cylindrical pressure vessel, like a McKibbons Actuator, the effect of hoop stress from fluid pressure dominates the tensile stress in the individual fibers. It is established that $$T = \frac{PDd}{2\sin(\theta)} \quad (1)$$

where P, D, d, and θ are the fluid pressure, actuator tube inner diameter, fiber diameter, and weave angle respectively. As expected, the hoop stress, and therefore the tension, increase as a function of actuator diameter. The relationship for the peak contractile force (F) of a McKibbons style actuator can be expressed as:

$$F = \frac{\pi}{4} D_o^2 P \frac{1}{\sin^2(\theta)} (3 \cos^2(\theta_0) - 1) \qquad (2)$$

where $\theta_o$ and $D_o$ represent the weave angle and diameter of the actuator while at rest. For a given fiber, with diameter d and max tensile stress $\sigma_t$, and initial weave angle $\theta_o$ we can use Eqns. (1) and (2) to determine the maximum allowable fluid pressure as a function of diameter $D_o$.

$$T_{max} = \frac{\pi}{4} \sigma_t d^2 \qquad (3)$$

$$P_{max} = T_{max} \frac{\sin(\theta_o)}{2Dd} \qquad (4)$$

Substituting $P_{max}$ into (2) allows for calculation of the peak contractile force $F_{max}$ as a function of diameter. Here, we consider the bundle of McKibbons actuator or BoMA approach where a single, large actuator can be replaced with multiple smaller actuators. By using smaller cylinders, a significantly higher fluid pressure can be used. Let t be the thickness of the actuator tube and fibers, so that the outer diameter of the actuator is D+t. Then, we can calculate the peak contractile stress as, $$\sigma_{max} = \frac{4F_{max}}{\pi(D+t)^2} \qquad (5)$$

Using sample system parameters for θ, d, and t, and the tensile strength for high strength polyethylene, FIG. 7 shows the peak contraction stress over a range of possible tube diameters. Note the peak near D=0.6 cm, which illustrates that the tube diameter at which the greatest force density can be achieved. In a real system, cylinders can only be close packed to overall density of 78%, so there is a slight advantage to using a single McKibbons actuator. However, as seen in the figure, this 22% difference is small when compared with the improvement in force density from using multiple cylinders. When compared with a single actuator with a 4 cm diameter, the BoMA approach with multiple 0.6 cm diameter actuators more than doubles the potential force density.

Hydraulics also enables important advantages for replicating the principle of co-contraction in biarticulate, flexor/ extensor muscle groups. Co-contraction has been shown to perform multiple functions in humans and animals, including a reduction of variability in reaching movements through increased stiffness produced by muscle activation and robustness to perturbations and an increase in joint impedance for greater limb stability, the quick generation of torque, and compensation for torque components orthogonal to desired trajectories.

In the BoMA approach, the stiffness inherent to the incompressible hydraulic fluid allows for precise control of a manipulator or leg through co-activation; for example, differences in simultaneous agonist (biceps brachii) contraction and antagonist (triceps brachii) contraction determine the position of the forearm. Isometric force can be determined by summing antagonist muscle torques; stiffness and torque can thus be controlled independently. This stiffness can be dynamically increased or decreased according to task requirements; greater stiffness allows for more precise control, while decreased stiffness enables more compliance. Additionally, the parallel elastic element in musculature acts as a lightly damped, non-linear spring which is the primary source for the passive tension (i.e., compliance) under eccentric loads which facilitates the contractile element's return to resting length. The elastic sheath of the fibers will provide some of this passive tension.

Hydraulics will inherently provide the remainder of damping using valves with adjustable orifices to produce a damping force proportional to the speed of movement. Since the biological tendon may contribute a great portion of compliance and therefore affect stiffness during locomotion, elasticity should be adjustable. Such stiffness will need to be counterbalanced with sufficiently high-bandwidth active and passive compliance to provide robustness to collisions and to maximize safety around humans. Thus, a key design characteristic of the BoMA approach is a range of compliance in both spring and damping characteristics. Approaches to compliance can be divided into two categories: passive and active. Passive approaches use the natural characteristics of materials to achieve spring and damping effects. Active compliance, on the other hand, is achieved by moving the actuator in a way that mimics a desired compliance.

Previously developed active approaches, such as the Series-Elastic Actuator use an actuator and tight control loop to mimic compliance of passive materials. In this approach, basic compliance is achieved through placement of spring between actuator and load; a linear potentiometer used to measure the spring's length provides force sensing that is combined with position sensors to facilitate rapid adjustments for desired position, velocity, springiness and damping gains. The series-elastic principle can be implemented using a hydraulic actuator that features low impedance and backdriveability; accordingly, the BoMA approach will be backdriveable.

For the BoMA approach, passive compliance is achieved through a number of means, including: the natural elasticity of the contractile sheath of the BoMA fibers, which provides a small restoring force back to resting length; through the elastic "tendons" arranged in series with the BoMA clusters, connecting them to the robot skeleton; through co-contraction control policies using adjustable stiffness; and through scalable actuation of individual fibers within clusters, exploiting the compliance of the surrounding unpressurized actuator material.

The actuators and mechanical muscles 10 described above can be used in a wide variety of applications extending beyond traditional robotics. For example, in accordance with illustrative embodiments the invention, the above described actuators or mechanical muscles 10 can be implemented as part of a body worn apparatus 20 that performs one or more a plurality of functions. Those functions can include, among other things, 1) enhancing the natural muscle strength of the human being (e.g., a so-called "muscle suit"), 2) assisting the human being in their normal breathing (e.g., acting as a respirator and/or providing CPR), 3) massaging natural muscles of a living being (e.g., a human being), 4) providing dynamic back support, 5) cooling or warming a living being or inanimate object, and 6) use for military and firefighting applications.

To those ends, FIG. 8 schematically shows a person wearing a body worn apparatus 20 configured in accordance with illustrative embodiments of the invention. In a complementary fashion, FIG. 9 schematically shows a backside view of the same person and body worn apparatus 20. It should be reiterated that these drawings are mere schematic representations and not intended to imply that all embodiments are oriented and configured as shown. Moreover, the body worn apparatus 20 also may be configured to be worn by non-human users (e.g., a horse or a dog). Discussion with regard to a human being thus is for simplicity and not intended to limit all embodiments of the invention. Those skilled in the art therefore should consider these figures as a starting point for expanding various options commensurate with the scope of the appended claims.

Among other things, the body worn apparatus 20 may take the form of a wearable article. For example, the article may be in the form of a garment having one or several pieces (e.g., a shirt and pants combination, or a single body suit), a member with some attachment mechanism (e.g., straps with Velcro to secure the member to the user's body), or some other device configured to be worn by a living being. Despite the form it takes, the body worn apparatus 20 has some type of the substrate 21 for supporting and accurately positioning the actuators/mechanical muscles 10. As such, it should be sized and configured to be secured with a living being. When the wearable article takes on the form of a garment, for example, the substrate 21 may be formed primarily from a flexible material, such as a composite material having fabric and advanced materials for supporting the various structures. For example, in that case, the substrate 21 may include a sleeve 22 or similar apparatus sized and oriented to receive the limb (e.g., arm or leg) of a living being (e.g., the arm of a human being). In fact, that type of body worn apparatus 20 also may have a main portion sized and oriented to receive the torso of a person. Despite the form it takes, the substrate 21 should be sufficiently strong to support its components, while not unduly limiting movement of the user.

Placement of the artificial muscles 10 typically dictates at least part of their intended function. To that end, FIGS. 8 and 9 schematically show placement of some components, including artificial muscles 10, in accordance with various embodiments the invention. As shown, the body worn apparatus 20 of those figures includes a single body suit having mechanical muscles 10 positioned at specified locations across the substrate 21. These muscles 10, which preferably are bundled as described above, may be considered as being formed in different groups depending upon the function. It should be noted, however, that although muscle bundles 12 are discussed as being in "groups," some groups may have a single muscle bundle 12 only. Accordingly, discussion of groups of muscle bundles 12 is but one of a number of different embodiments of the invention.

A first group of muscles 10 (referred to a "first muscle group 24") augments the natural muscle strength of the user. For example, this muscle grouping may enable a user to perform an unlimited number of chin-ups, or lift 2 to 3 times more weight than without the body worn apparatus 20. Accordingly, the bundles of muscles 10 (also referred to as "muscle bundles 12") are positioned strategically near the user's major natural muscle groups. The embodiment shown in the figures shows two of many such strategic locations; namely, across the elbow and knee joints 26A and 26B. Specifically, the first muscle group 24 has muscle bundles 12 that enhance the strength and ability of the user as they hinge/pivot/rotate their elbow joint 26A and/or knee joint 26B.

It should be noted that when used with reference to a joint, the terms "pivot, "hinge," and rotate" may be used herein generally synonymously as meaning "to move the joint in its normal manner of moving, such as its natural hinging motion." For example, the user may be considered to move or hinge or rotate or pivot the elbow joint 26A when moving the lower arm relative to the upper arm in a natural manner, such as by curling a dumbbell.

To those end, as shown in FIG. 8, one set of muscle bundles 12 extends across the user's elbow joints 26 and, consequently, is referred to as "artificial biceps." The body worn apparatus 20 further has appropriate anchor points to secure the artificial biceps in multiple locations along the arm region of the body worn apparatus 20. For example, Each of the artificial biceps muscles may be secured to the substrate 21 at its end region, and at pre-specified locations across its length.

In a corresponding manner, FIG. 9 shows bundles of mechanical muscles 10 positioned on the back side of the elbow joint 26A to augment the user's triceps (referred to herein for simplicity as "artificial triceps"). Like the artificial biceps, the body worn apparatus 20 has appropriate anchor points to secure the artificial triceps. Like natural human triceps, artificial triceps effectively are configured to rotate/hinge/pivot the arm about the elbow joint 26A in a direction that is generally opposite to that of the biceps. These artificial biceps and artificial triceps are selectively actuated as described above to most efficiently enhance the strength of the user about the elbow joint 26A. Stated another way, the artificial muscle bundles 12 may work alone (e.g., the artificial biceps alone), or in combination (e.g., the artificial biceps and artificial triceps cooperating) to perform a desired function.

The artificial muscle bundles 12 in the leg region of the body worn apparatus 20 are similarly anchored and coordinated to provide the same or similar enhanced strength functionality as described above with regard to the artificial biceps and artificial triceps. Specifically, the muscle bundles 12 shown in FIGS. 8 and 9 in the leg region augment the user's natural muscle strength about the knee joint 26B. Of course, it should be reiterated that various embodiments position muscle bundles 12 across various other joints or in other locations to enhance strength in those regions. For example, artificial muscles 10 can be placed across shoulder joints, wrist joints, finger joints, ankle joints, and across the body core/general abdominal area. Accordingly, discussion primarily of the elbow and knee joints 26A and 26B is for simplicity only and not intended to limit various embodiments.

When used to augment strength, the body worn apparatus 20 can have any of a wide variety of different applications. Among other applications, the body worn apparatus 20 can be used for military, law enforcement, construction, factory work, therapeutic, handicap assisting, and other applications, to name but a few.

As noted above, in addition to enhancing and augmenting the user's natural strength, the body worn apparatus 20 also can assist the human being in their normal breathing (e.g., acting as a respirator and/or providing CPR). To that end, the substrate 21 supports a second group of artificial muscle bundles 12 (referred to as "second muscle group 28") in its chest region/portion as shown schematically in FIG. 8. More specifically, this second group 28 should be positioned to correspond with the chest region of the user for assisting normal breathing. When needed, the bundle of artificial muscles 10 in the chest region therefore may periodically actuate to assist the user's breathing processes. This can be a continuous, periodic actuation, configured specifically to assist breathing.

FIG. 9 shows yet another application, in which a third group of artificial muscle bundles 12 (referred to as a "third muscle group 30") are strategically positioned to massage specified natural muscle groups of the user. This third group 30 is schematically shown in the back of the user, which is a very common area for massaging. Of course, muscle bundles 12 may be in any of a number of other regions to provide a massage. For example, those additional regions may include the legs, the arms, shoulders, feet, hands, neck, and the torso, to name but a few.

The third muscle group 30 shown in FIG. 9 also may provide dynamic back support to the user. The substrate 21 therefore may position artificial muscle bundles 12 in a back region to control substrate stiffness/flexibility. For example, a person riding on a long car ride may vary the lumbar support in that region of the body worn apparatus 20. The level and amount of support may be changed automatically, or manually. In fact, some of the artificial muscle bundles 12 used for other purposes (e.g., those discussed above with regard to massaging) can provide one or more functions, such as massaging, automatic breathing support, and dynamic back support, among other things.

As described above, the artificial muscle bundles 12 are fluid activated. For example, some of the artificial muscle bundles 12 may be activated by directing a liquid, such as water, into and out of the individual activation elements. The inventors discovered that if positioned and configured appropriately, in addition to controlling muscle actuation, this fluid can assist in controlling the user's temperature. For example, water used actuate the artificial muscles 10 can be chilled and placed in close thermal contact with the user to reduce the risk that the user may overheat when in a hot environment (e.g., in a desert or in a burning building). As another example, that same water can also be heated to keep the user warm in a cold environment (e.g., during prolonged hikes in cold geographies).

To those ends, the body worn apparatus 20 may include a temperature controller 32 having the logic and structure for selectively cooling and heating the fluid directed to and from the artificial muscle bundles 12 via various fluid transport tubes and channels 34 formed on or in the substrate 21. Among other things, the temperature controller 32 may have direct contact or noncontact heating and cooling mechanisms for controlling fluid temperature. Some embodiments may have heating mechanisms and no cooling mechanisms. Other embodiments may have cooling mechanisms and no heating mechanisms. Still other embodiments may have both types of mechanisms.

The temperature controller 32 may be completely integrated on the body worn apparatus 20, or distributed between the body worn apparatus 20 and some exterior component. The exterior component may be securable to the body worn apparatus 20, or remain separate.

The tubes and channels 34 distributing the fluid (shown generally in FIGS. 8 and 9 merely as arrows) about the substrate 21 are strategically positioned to selectively contact the user in specific locations. They may take the most direct path to the artificial muscles 10, or take a longer path (e.g., in a sinusoidal path) to cool or heat more area of the user's body. The body contact of the tubes and channels 34 may be direct to the user's skin, or may be through some other element, such as a thin layer of material protecting the user's skin from the anticipated fluid temperatures.

This embodiment thus produces a heat transfer relationship between the user and the fluid, which can improve operation of other functions. For example, when used to cool the user, such as in a firefighting application, coolant fluid returning to the temperature controller 32 is warmer due to its cooling contact with the user. This warmer water may be used to help other processes in a subsequent heat exchange relationship.

All or portions of the body worn apparatus 20 can include a thermal insulating material that is exterior to the artificial muscles 10. For example, the insulating material can assist in keeping heat near the user, or assist in keeping the user cool. This material can be on the interior, exterior, or both.

The body worn apparatus 20 also may be configured to protect the user's safety in situations where the risk of injury from fire is high. Among others, this may include situations such as firefighting, hazardous material handling, and bomb defusing. To protect the user, some or all of the components of the body worn apparatus 20 can be formed from fire resistant/retardant material. For example, the body worn apparatus 20 may have a layer of fire resistant material on its most exterior surface, covering the artificial material and other components. Such material may include any of those materials used in clothing or other related applications and are commonly known in the art.

Accordingly, illustrative embodiments extend use of the artificial muscles/activation elements 10 beyond robotics and into a body worn apparatus 20 that can have any of a variety of helpful functions. The body worn apparatus 20 can have all of the noted functions, one of the noted functions, or some other combination of functions. For example, some embodiments may have the augmented strength function alone, while other embodiments may have the augmented strength function, cooling function, and fire resistant function.

Although the description above contains many specific examples, these should not be construed as limiting the scope of the embodiments of the present disclosure but as merely providing illustrations of some of the presently preferred embodiments of this disclosure. Thus, the scope of the embodiments of the disclosure should be determined by the appended claims and their legal equivalents, rather than by the examples given.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the embodiments of the present disclosure.

I claim:

1. A method of assisting a living being with an apparatus substantially in the form of a wearable garment, comprising:
    providing a substantially soft, pliable apparatus to be worn by an individual, the apparatus including a plurality of elongate, pliable, artificial muscle style, incompressible hydraulic fluid activation elements arranged in at least one bundle of activation elements, the activation elements being arranged parallel in side-by-side relationship with respect to their lengths, the elongate activation elements having a diameter between 0.4-0.8 cm so that the bundle of activation elements has about twice the force density of a single activation element having a diameter at least five times greater than the activation elements in the bundle;

providing a substantially soft, pliable substrate for mounting of the at least one bundle of activation elements to likewise be worn by an individual and for cooperative engagement with a body portion of an individual;

providing an incompressible hydraulic fluid pump system for independent and selective activation of each activation element of the bundle to vary a force applied by the bundle and the substrate to the individual;

anchoring both ends of each activation element of the bundle to the substrate so that when activated by the hydraulic fluid pump system a desired number of activation elements expand outwardly along their lengths to thereby contract and provide a contraction force to the substrate; and activating a desired number of activation elements to provide the force to the individual.

* * * * *